US012576219B2

(12) United States Patent
Yang et al.

(10) Patent No.: US 12,576,219 B2
(45) Date of Patent: Mar. 17, 2026

(54) SPRAYING ASSEMBLY

(71) Applicant: WUXI NEST BIOTECHNOLOGY CO., LTD, Wuxi (CN)

(72) Inventors: Weidong Yang, Wuxi (CN); Feng Chen, Wuxi (CN); Xiaojian Zhu, Wuxi (CN)

(73) Assignee: WUXI NEST BIOTECHNOLOGY CO., LTD, Wuxi (CN)

( * ) Notice: Subject to any disclaimer, the term of this patent is extended or adjusted under 35 U.S.C. 154(b) by 791 days.

(21) Appl. No.: 17/804,564

(22) Filed: May 30, 2022

(65) Prior Publication Data

US 2022/0288330 A1    Sep. 15, 2022

Related U.S. Application Data

(63) Continuation of application No. PCT/CN2020/132758, filed on Nov. 30, 2020.

(30) Foreign Application Priority Data

Nov. 28, 2019    (CN) .......................... 201911190535.9

(51) Int. Cl.
  *A61M 11/00*        (2006.01)
  *B05B 11/00*        (2023.01)
(52) U.S. Cl.
  CPC ....... *A61M 11/007* (2014.02); *B05B 11/0035* (2013.01)

(58) Field of Classification Search
  CPC ........ A61M 11/007; A61M 2202/0468; A61M 2205/02; A61M 2207/00; A61M 15/08; B05B 11/0035; B05B 11/007; B05B 11/02; B05B 1/3436
  See application file for complete search history.

(56) References Cited

U.S. PATENT DOCUMENTS

| 5,064,122 | A | * | 11/1991 | Kamishita | ............. | B05B 1/3436 |
| | | | | | | 239/491 |
| 6,450,216 | B1 | | 9/2002 | Stradella | | |
| 9,174,010 | B2 | | 11/2015 | Vedrine | | |
| | | | (Continued) | | | |

FOREIGN PATENT DOCUMENTS

| CN | 104524674 A | 4/2015 |
| CN | 104815365 A | 8/2015 |
| | (Continued) | |

*Primary Examiner* — James D Ponton
(74) *Attorney, Agent, or Firm* — Kilpatrick Townsend & Stockton LLP

(57) ABSTRACT

A spraying assembly, including an atomizer, a sprayer and a rubber plug, and an atomizer inner cavity and an atomizer channel located below the atomizer inner cavity are provided in the atomizer, an atomizer end (130) is included in a lower part of the atomizer, and a side wall of the atomizer end is provided with at least one opening; the rubber plug is located at a bottom end of the atomizer inner cavity, an upper end of the rubber plug is provided with an umbrella-shaped boss, an annular cavity is formed between a lower end of the rubber plug and an inner wall of the atomizer, the rubber plug is provided with at least one longitudinal notch along a circumferential direction, and the bottom end of the atomizer inner cavity is provided with at least one notch; the sprayer includes a nozzle.

12 Claims, 9 Drawing Sheets

(56) References Cited

U.S. PATENT DOCUMENTS

| | | | |
|---|---|---|---|
| 2002/0174865 A1 | 11/2002 | Gatton, Jr. et al. | |
| 2011/0049265 A1* | 3/2011 | Vedrine | A61M 11/00 |
| | | | 29/525 |

FOREIGN PATENT DOCUMENTS

| | | | |
|---|---|---|---|
| CN | 106178238 | A | 12/2016 |
| CN | 106345044 | A | 1/2017 |
| CN | 107497036 | A | 12/2017 |
| CN | 109562237 | A | 4/2019 |
| CN | 208809294 | U | 5/2019 |
| CN | 208865022 | U | 5/2019 |
| CN | 110721373 | A | 1/2020 |
| CN | 211798072 | U | 10/2020 |
| EP | 0526824 | B1 | 6/1996 |
| WO | 2017021878 | A1 | 2/2017 |

* cited by examiner

SPRAYING ASSEMBLY

FIELD

The present disclosure relates to the field of medical consumables, in particular to a spraying assembly.

BACKGROUND

Pre-filling syringe is a new type of drug packaging developed in the 1990s abroad. After more than ten years of popularization and use, it plays a good role in preventing the spread of infectious diseases and the development of medical undertakings. The pre-filling syringe is mainly used for packaging and storage of high-grade drugs, as well as directly used for injection, surgical flushing or vaccination of ophthalmology, otology, orthopedics, etc.

The current pre-filling syringe adopts a form of subcutaneous injection, which causes certain pain and injury to patients and vaccinators, and often causes psychological trauma. Due to the popularity of vaccination in recent years, nasal spray is increasingly used to spray drugs into the nasal cavity of patients in the form of spray, to reduce the pain and discomfort of patients. Therefore, it is very important to keep the needle tube inner cavity of the spraying device in vacuum state, as well as avoid leakage and overflow, during filling, transportation and not using.

Therefore, there is a need in the art for an improved spraying assembly.

SUMMARY

A brief overview of one or more aspects is given below to provide a basic understanding of these aspects. This overview is not a detailed overview of all conceived aspects, and is not intended to identify the key or decisive elements of all aspects or to attempt to define the scope of any or all aspects. The only purpose thereof is to give some concepts of one or more aspects in a simplified form as a preface to a more detailed description given later.

According to one aspect of the present disclosure, a spraying assembly is provided, which comprises an atomizer, a sprayer and a rubber plug. An atomizer inner cavity and an atomizer channel located below the atomizer inner cavity are provided in the atomizer. An atomizer end is comprised in a lower part of the atomizer. A side wall of the atomizer end is provided with at least one opening. The rubber plug is located at a bottom end of the atomizer inner cavity. An upper end of the rubber plug is provided with an umbrella-shaped boss. An annular cavity is formed between a lower end of the rubber plug and an inner wall of the atomizer. The rubber plug is provided with at least one longitudinal notch along a circumferential direction to connect the annular cavity and space above the rubber plug. The bottom end of the atomizer inner cavity is provided with at least one notch to connect the atomizer channel and the annular cavity. The sprayer comprises a nozzle. The atomizer end of the atomizer extends into a nozzle inner cavity of the nozzle. The at least one opening on the atomizer end connects the atomizer channel of the atomizer to the nozzle inner cavity. A bottom of the nozzle is provided with an umbrella-shaped inner cavity. An outlet hole is arranged in center of a head of the umbrella-shaped inner cavity.

In an embodiment, diameter of the lower end of the rubber plug is smaller than that of the atomizer inner cavity to form the annular cavity.

In an embodiment, a middle part of the rubber plug is provided with a convex part along an outer circumference, and the convex part contacts with an inner wall of the atomizer inner cavity.

In an embodiment, the convex part is a hemispherical or tapered convex structure.

In an embodiment, the rubber plug is made of elastic material.

In an embodiment, the elastic material comprises isobutylene isoprene rubber, nitrile butadiene rubber, silica gel, rubber, TPE, TPU or PVC.

In an embodiment, a profile angle of a cross section of the umbrella-shaped boss is 142°±37°.

In an embodiment, a circle of fastening section is arranged above the atomizer end, and an outer side of the fastening section is interference fit with an inner wall above the spray nozzle of the sprayer to realize sealing.

In an embodiment, a circle of convex part is arranged above the fastening section of the atomizer along an outer circumference. The inner wall of the sprayer is provided with at least one convex buckle, and the buckle and the convex part realize the closure of the atomizer and the sprayer.

In an embodiment, a spiral boss is arranged around the umbrella-shaped inner cavity on an inner end surface of the nozzle.

In an embodiment, the spraying assembly further comprises: a needle tube, a front end of which extends into the atomizer inner cavity of the atomizer and butts against the umbrella-shaped boss of the rubber plug, and a liquid outlet of the needle tube is blocked by the umbrella-shaped boss; and a push rod, arranged in the needle tube, and installing a piston at a front end thereof.

In an embodiment, the spraying assembly further includes a protective cap for protecting the nozzle, and a location limiter is arranged between a tail end of the needle tube and a tail end of the push rod.

BRIEF DESCRIPTION OF THE DRAWINGS

The above embodiments of the present disclosure will be better understood after reading the detailed description of the embodiments of the present disclosure in conjunction with the following figures. In the figures, components are not necessarily drawn to scale, and components having similar related features may have the same or similar reference numerals.

REFERENCE SIGNS

Figure 1A:
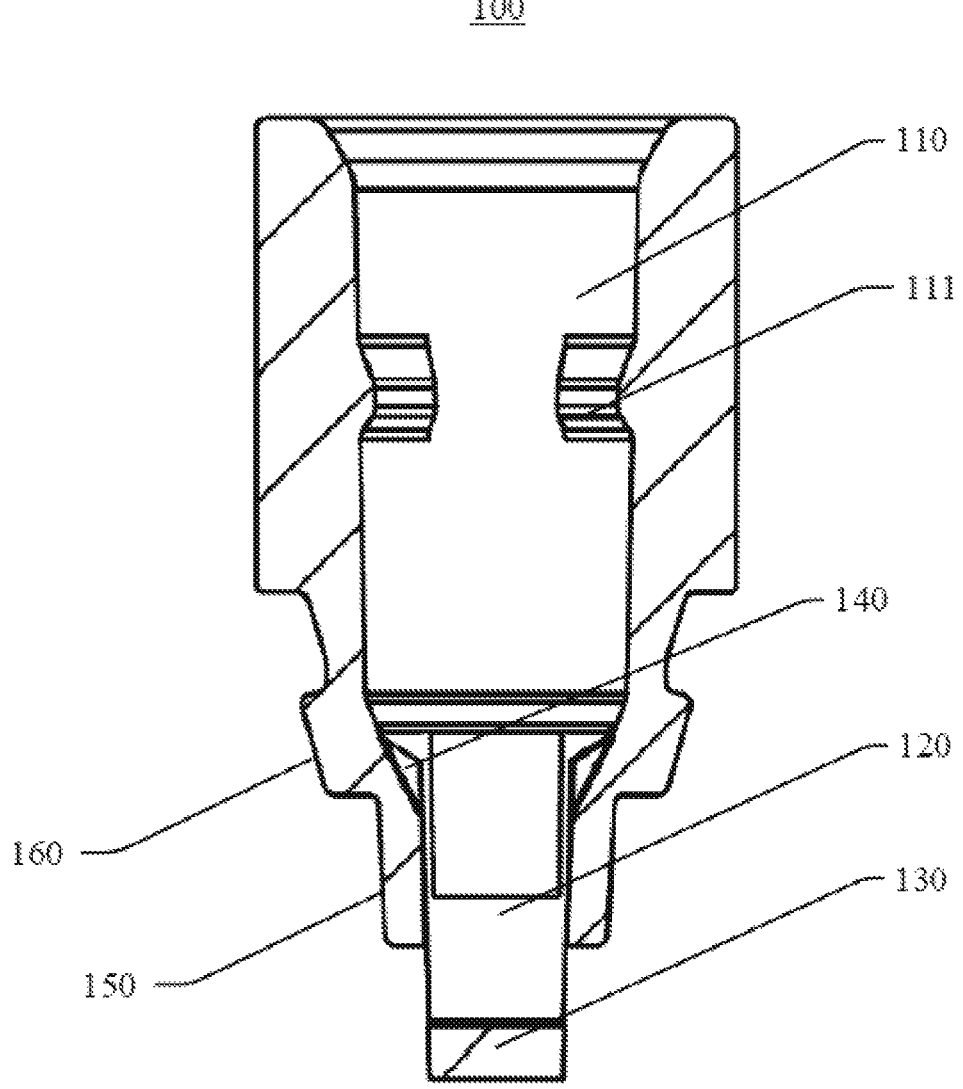
FIG. 1A shows a sectional view of the atomizer of the spraying assembly according to one aspect of the present disclosure.

100: atomizer
110: atomizer inner cavity
111: buckle
120: atomizer channel
130: atomizer end
131: opening
140: notch
150: fastening section
160: convex part
200: rubber plug
210: annular cavity
220: convex part
230: umbrella-shaped boss
231: tip
240: longitudinal notch
300: sprayer
310: nozzle
320: umbrella-shaped inner cavity
321: outlet hole
330: buckle
400: needle tube
410: liquid outlet
420: convex part
500: push rod
510: piston
600: location limiter
700: protective cap

DETAILED DESCRIPTION OF EMBODIMENTS

The following description is given regarding embodiments of the present disclosure and combine it into a specific application background. Various variants and various uses in different applications will be readily apparent, and the general principles defined herein can be applied to a wide range of embodiments. Thus, the present disclosure is not limited to the embodiments given herein, but should be granted the broadest scope consistent with the principles and novel features disclosed herein.

In the following detailed description, many specific details are set forth to provide a more thorough understanding of the present disclosure. In other words, the well-known structures and devices are shown in the form of block diagram without detailed display, to avoid blurring the present disclosure.

Unless otherwise directly stated, all features disclosed in this specification (including any attached claims, abstracts and drawings) can be replaced by alternative features for the same, equivalent or similar purposes. Therefore, unless otherwise expressly stated, each feature disclosed is only one example of a set of equivalent or similar features.

It should be noted that when used, signs such as left, right, front, rear, top, bottom, positive, negative, clockwise and counterclockwise are only used for convenience, and do not imply any specific fixed direction. In fact, they are used to reflect the relative position and/or direction between various parts of the object. In addition, the terms "first" and "second" are only used for descriptive purposes and cannot be understood as indicating or implying relative importance.

In the description of the present disclosure, it should be noted that unless otherwise clearly specified and limited, the terms "installation", "connect" and "connection" should be understood in a broad sense. For example, it can be fixed connection, removable connection or integrated connection; mechanical connection or electrical connection; as well as direct connection, indirect connection through an intermediate medium, or connection within two components.

It should be noted that in the case of use, terms such as further, preferably, furthermore and more preferably is a simple beginning to elaborate another embodiment based on the above embodiment. The combination of the content of the further, preferably, furthermore or more preferably and the above embodiment is a complete composition of another embodiment. Another embodiment can be composed by arbitrarily combining the same embodiment with several further, preferably, furthermore or more preferably embodiments provided following.

The present disclosure is described in detail below in combination with the accompanying drawings and specific embodiments. It should be noted that the aspects described below in connection with the accompanying drawings and specific embodiments are only exemplary and should not be understood as limiting the scope of protection of the present disclosure.

Figure 1B:
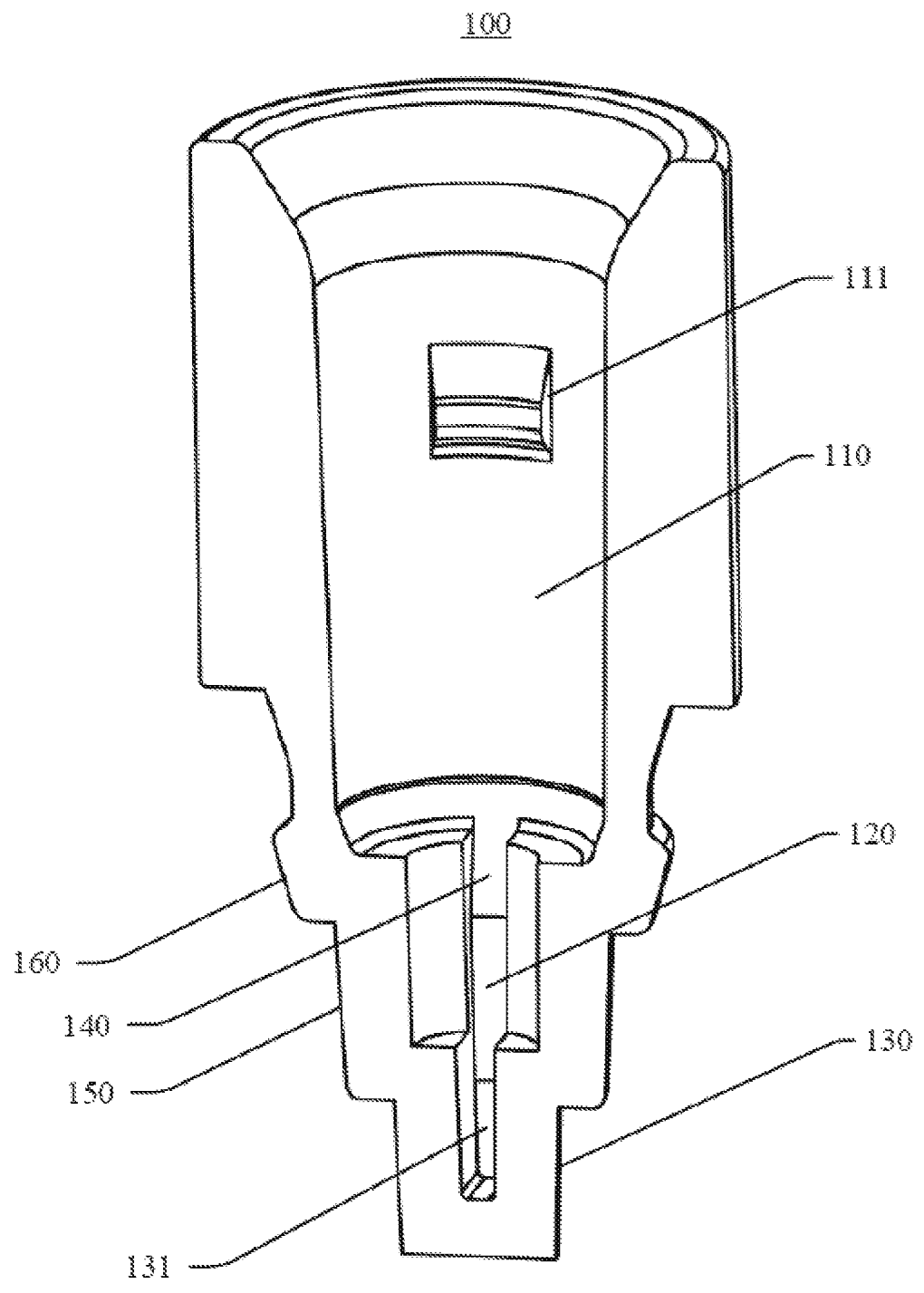
FIG. 1B shows a sectional view of the atomizer of the spraying assembly according to one aspect of the present disclosure from another visual angle.
Figure 1C:
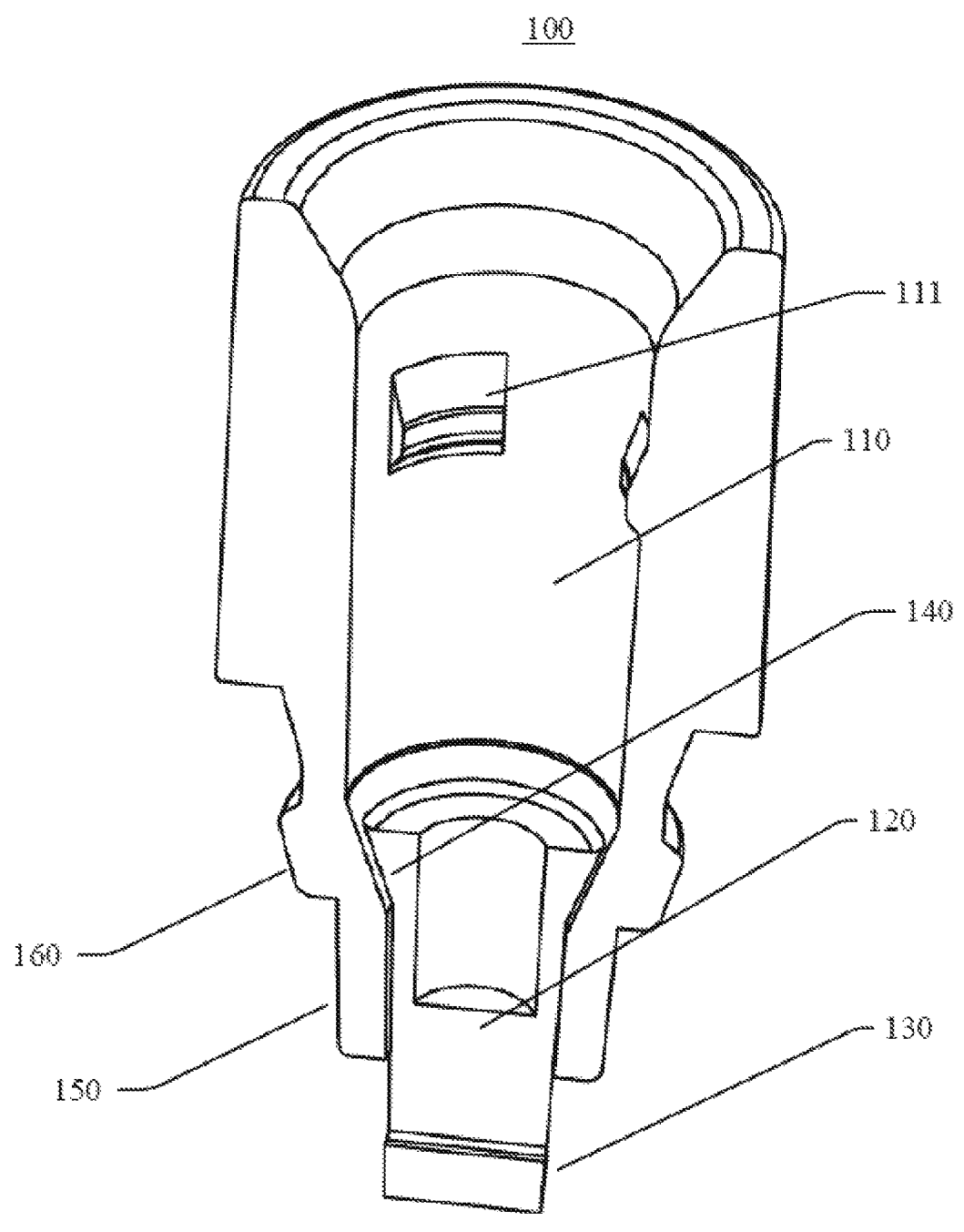
FIG. 1C shows a sectional view of the atomizer of the spraying assembly according to one aspect of the present disclosure from another visual angle.

FIG. 1A-1C shows a sectional view of the atomizer 100 of the spraying assembly according to one aspect of the present disclosure. As shown in FIG. 1A-1C, the atomizer 100 is in a tubular structure as a whole. An atomizer inner cavity 110 and an atomizer channel 120 located below the atomizer inner cavity 110 are opened inside the atomizer 100. The atomizer 100 includes an atomizer end 130 at a lower part, and at least one opening 131 is opened on a side wall of the atomizer end 130. Liquid medicine in the atomizer channel 120 can flow out of the atomizer end 130 through the opening 131 on the atomizer end 130. As an example, two opposite openings 131 are shown in FIG. 1A-1C.

At least one notch 140 is arranged at a bottom end of the atomizer inner cavity 110, which connects the atomizer channel 120 under the atomizer inner cavity 110 with the space of the atomizer inner cavity 110. As an example, two relative notches 140 are shown in the figures. The notches 140 may be oblique incisions, i.e. with an angle to the horizontal direction.

Figure 2A:
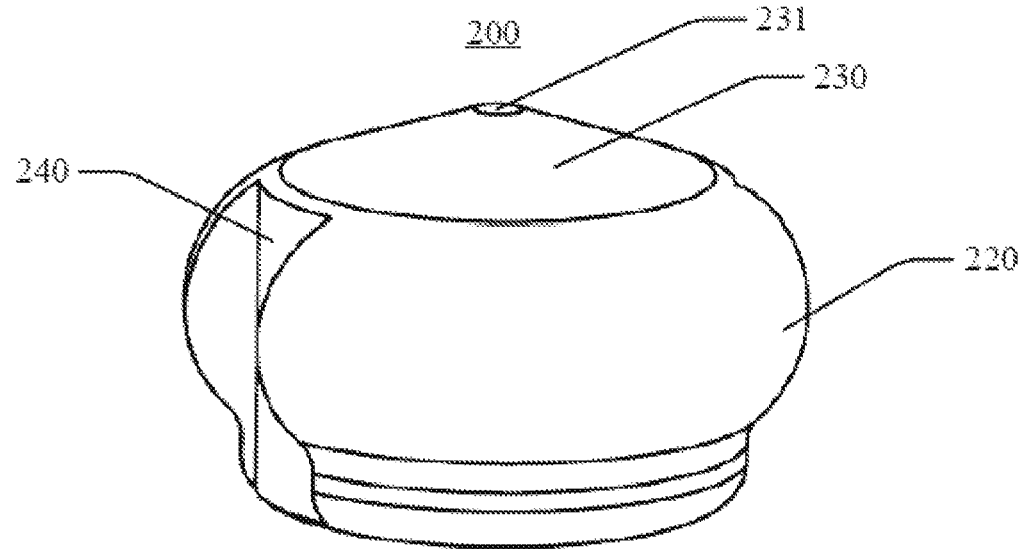
FIG. 2A shows a stereoscopic view of the rubber plug according to one embodiment of the present disclosure.
Figure 2B:
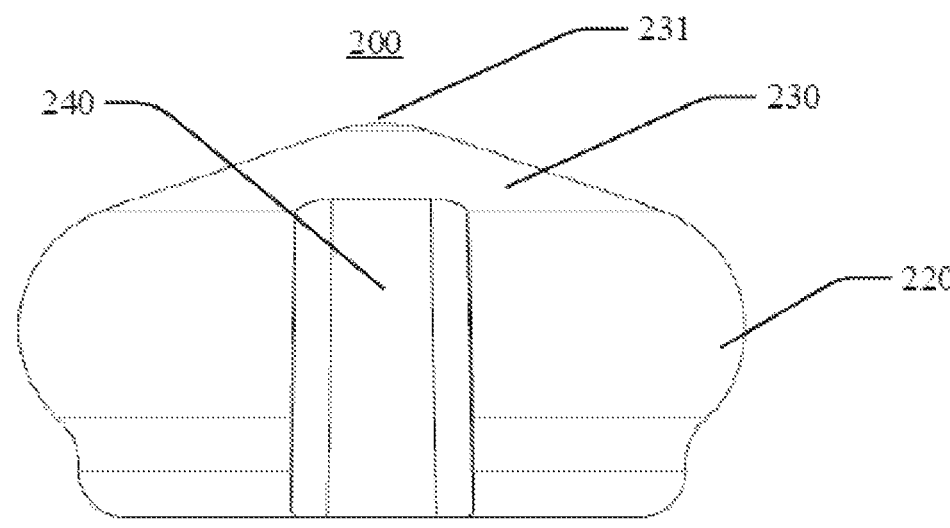
FIG. 2B shows a sectional view of the rubber plug according to one embodiment of the present disclosure.
Figure 3A:
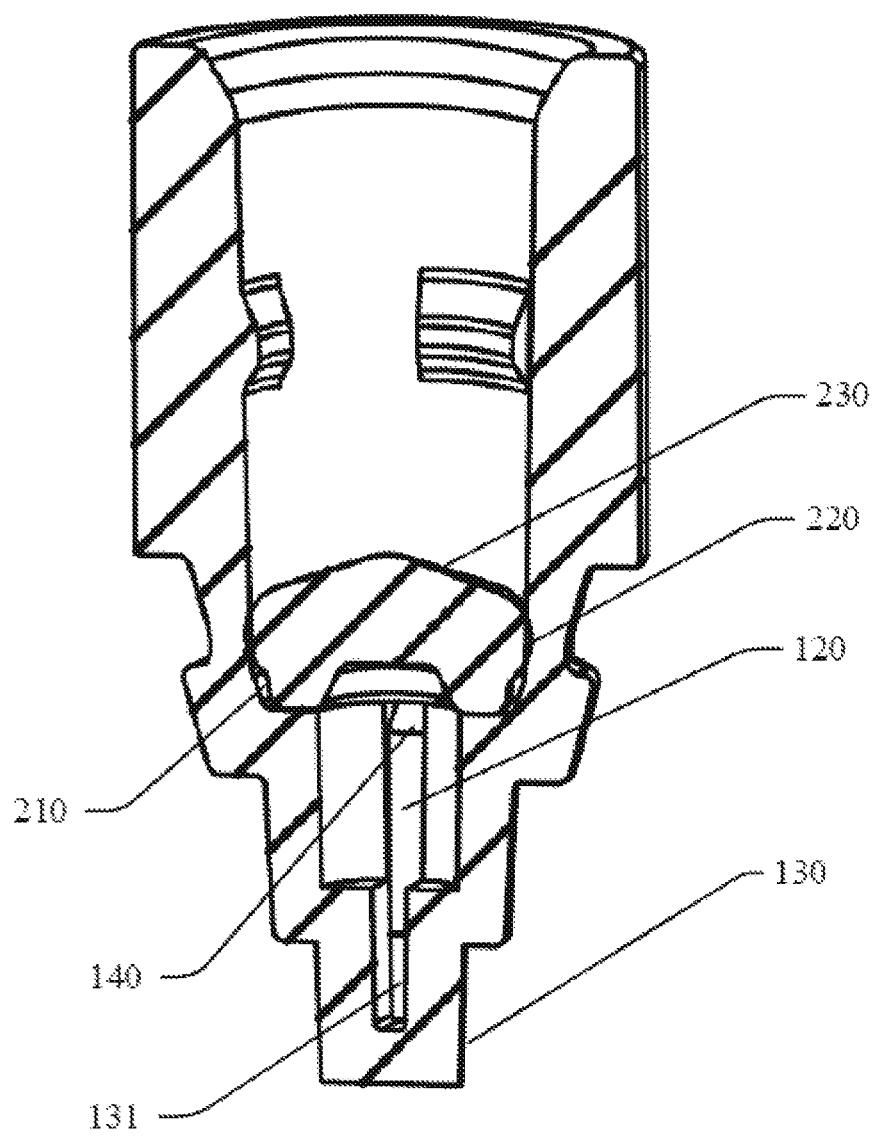
FIG. 3A shows a sectional view of the assembly of the rubber plug and the atomizer according to one embodiment of the present disclosure.
Figure 3B:
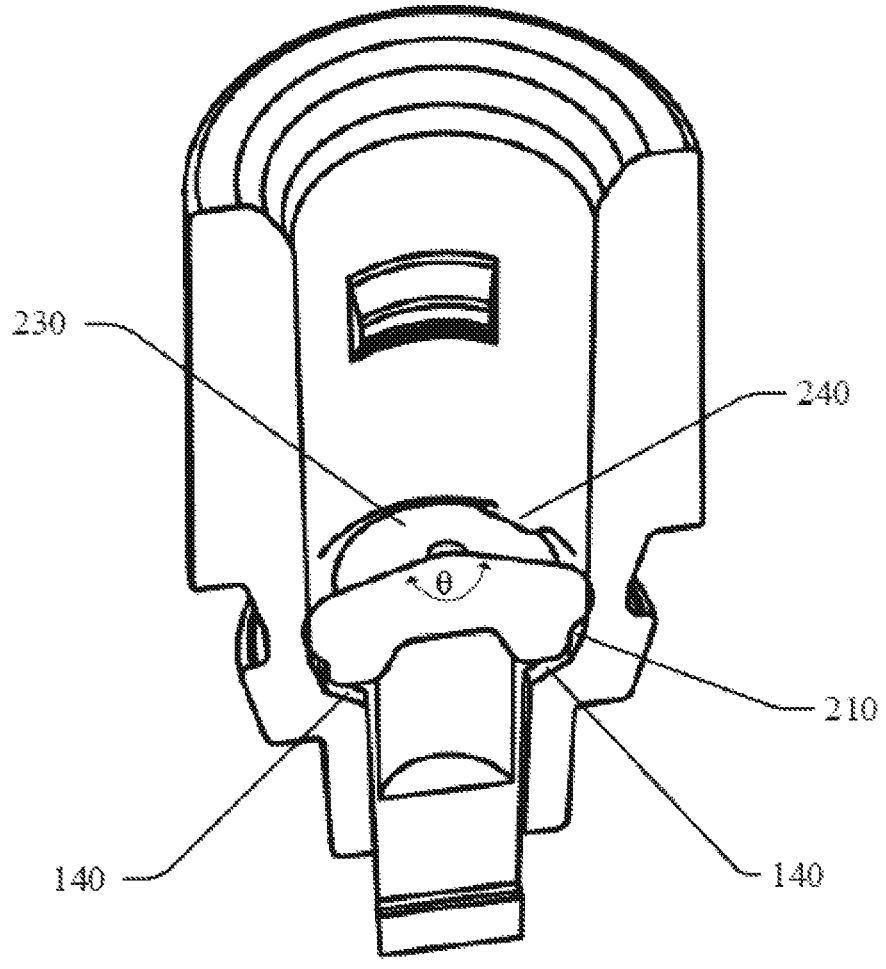
FIG. 3B shows a sectional view of the assembly of the rubber plug and the atomizer according to one embodiment of the present disclosure.

FIG. 2A and FIG. 2B respectively show a stereoscopic view and a sectional view of the rubber plug 200 according to one embodiment of the present disclosure. FIG. 3A and FIG. 3B respectively show a sectional view of a combination of the rubber plug 200 and the atomizer 100 according to one embodiment of the present disclosure.

As shown in FIGS. 3A and 3B, when used, the rubber plug 200 is placed in the atomizer inner cavity 110 of the atomizer 100, which is located at the bottom end of the atomizer inner cavity 110, and separates the space of the atomizer inner cavity 110 above the rubber plug from the space of the atomizer channel 120 under the rubber plug. A circle of annular cavity 210 around the rubber plug 200 is formed between the lower end of the rubber plug 200 and the inner wall of the atomizer inner cavity 110.

In an embodiment, the diameter of the lower end of the rubber plug 200 is smaller than the diameter of the atomizer inner cavity 110 in the same position, to form the annular cavity 210 between the two. In one embodiment, in the example shown in FIGS. 2A-2B and FIGS. 3A-3B, the middle part of the rubber plug 200 is provided with a convex part 220 along the outer circumference, which contacts with the inner wall of the atomizer inner cavity 110, and forms the annular cavity 210 under the convex part 220. In an embodiment, the convex part 220 may be a hemispherical or conical convex structure.

The upper end of the rubber plug 200 is an umbrella-shaped boss 230 with a tip 231 in the middle. In an embodiment, the umbrella-shaped boss 230 is a conical or arc convex structure, and the range of the profile angle θ in the cross-section, taking the tip 231 as the vertex, can be 142°±37°.

The rubber plug 200 may be made of elastic materials. In an embodiment, the elastic materials may include any suitable material that can deform under extrusion, such as nitrile butadiene rubber, silica gel, rubber, TPE, TPU or PVC.

The rubber plug 200 may be provided with at least one longitudinal notch 240 in a circumferential direction. The longitudinal notch 240 can connect the annular cavity 210 to a space above the rubber plug 200. In an embodiment, the longitudinal notch 240 may be in any suitable shape, such as arc, square, etc.

As shown in FIGS. 2A-2B and FIGS. 3A-3B, the notch 140 at the bottom end of the atomizer inner cavity 110 is connected with the annular cavity 210. Since the notch 140 also leads to the atomizer channel 120, the atomizer channel 120 under the rubber plug 200 is connected with the annular cavity 210, and then the space above the rubber plug 200 is connected through the longitudinal notch 240.

Figure 4:
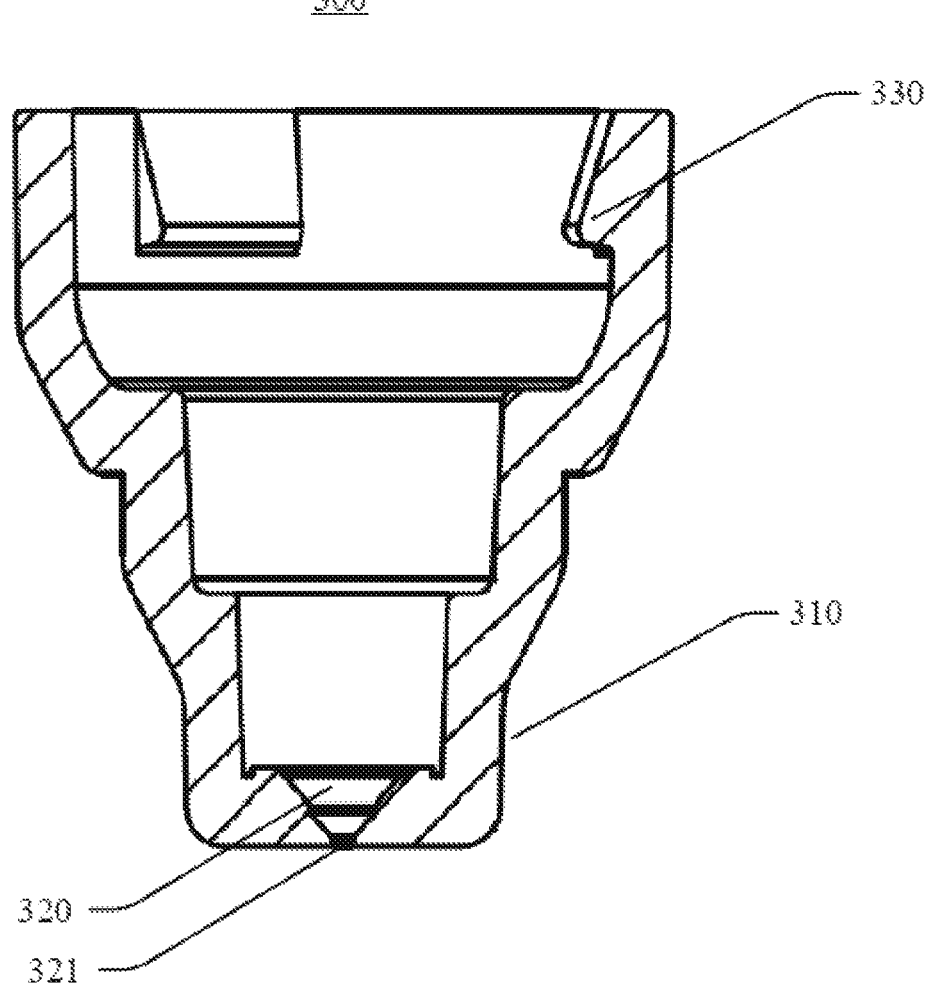
FIG. 4 shows a sectional view of the sprayer of the spraying assembly according to one aspect of the present disclosure.
Figure 5:
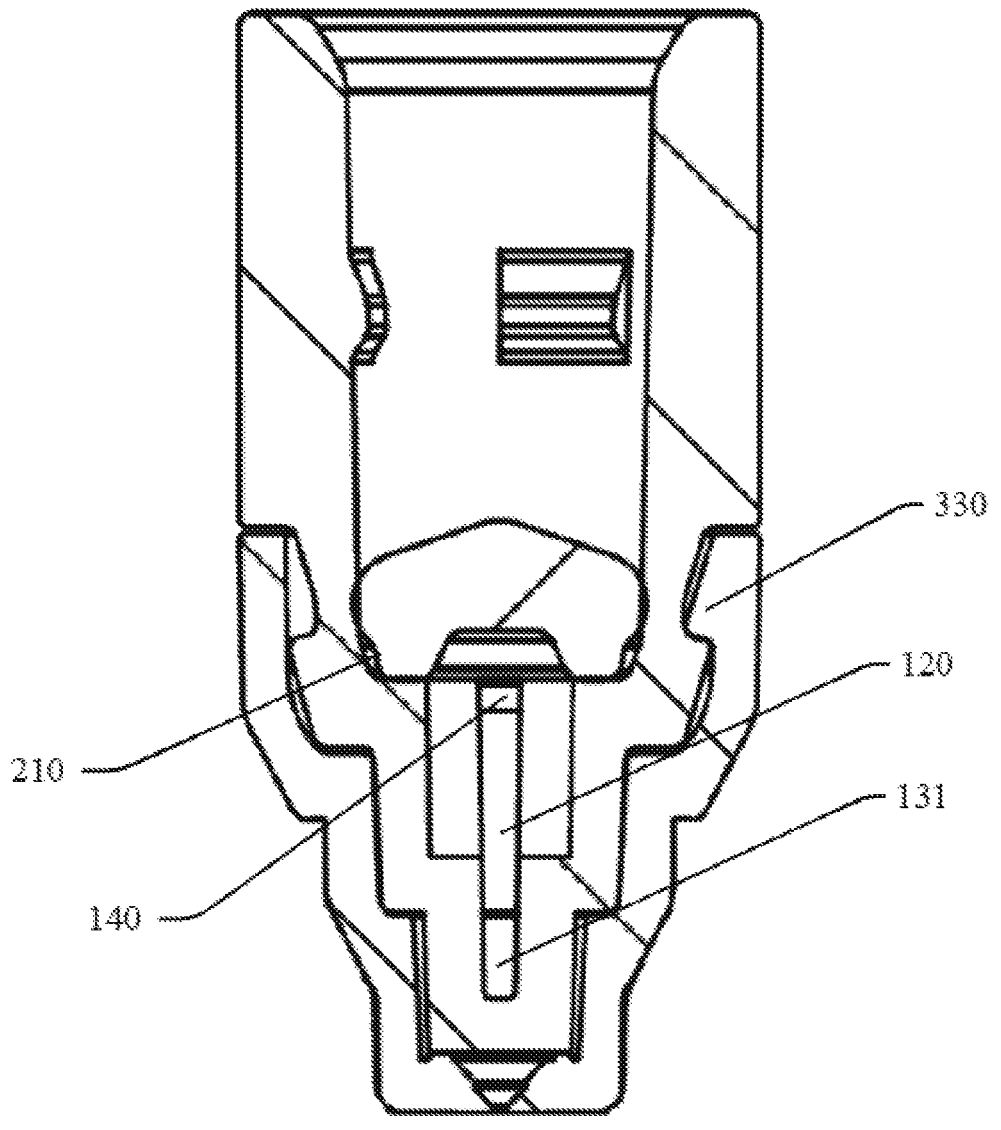
FIG. 5 shows a sectional view of the assembly of the rubber plug, the atomizer and the sprayer according to one aspect of the present disclosure.

FIG. 4 shows a sectional view of the sprayer 300 of a spraying assembly according to one embodiment of the present disclosure. FIG. 5 shows a sectional view of a combination of the atomizer 100, the rubber plug 200 and the sprayer 300 according to one embodiment of the present disclosure.

As shown in FIGS. 4-5, the sprayer 300 is hollow as a whole, and the lower end of the sprayer 300 may include a nozzle 310. The bottom of the nozzle 310 is provided with an umbrella-shaped inner cavity 320, and an outlet hole 321 is arranged in center of the head of the umbrella-shaped inner cavity 320. The umbrella-shaped inner cavity 320 penetrates from the inner end surface of the nozzle 310 to the outside for ejecting the liquid medicine. On the inner end surface at the bottom of the nozzle 310, spiral protrusions are arranged around the umbrella-shaped inner cavity 320, which is used to make the liquid medicine entering the umbrella-shaped inner cavity 320 in a spiral state.

During use, the lower part of the atomizer 100 is inserted into the interior of the sprayer 300, and the atomizer end 130 of the atomizer 100 extends into the inner cavity of the nozzle 310 of the sprayer 300. The front end surface of the atomizer end 130 may be buttressed with the spiral protrusion on the inner end surface.

In an embodiment, a circle of fastening section 150 may be arranged above the atomizer end 130 of the atomizer 100. Preferably, the outer surface of the fastening section 150 can be interference fit with the inner wall above the nozzle of the sprayer 300 to achieve sealing, to effectively control the overflow phenomenon. In one embodiment, adhesive may be used between the outer surface of the fastening section 150 and the inner wall above the nozzle of the sprayer 300 to achieve sealing.

In an embodiment, a circle of convex part 160 is arranged above the atomizer end 130 of atomizer 100 along the outer circumference. On the height corresponding to the convex part 160, at least one convex buckle 330 is arranged on the inner wall of the sprayer 300. The fit between the buckle 330 and the convex part 160 realizes the clamping and positioning between the atomizer 100 and the sprayer 300.

Figure 6:
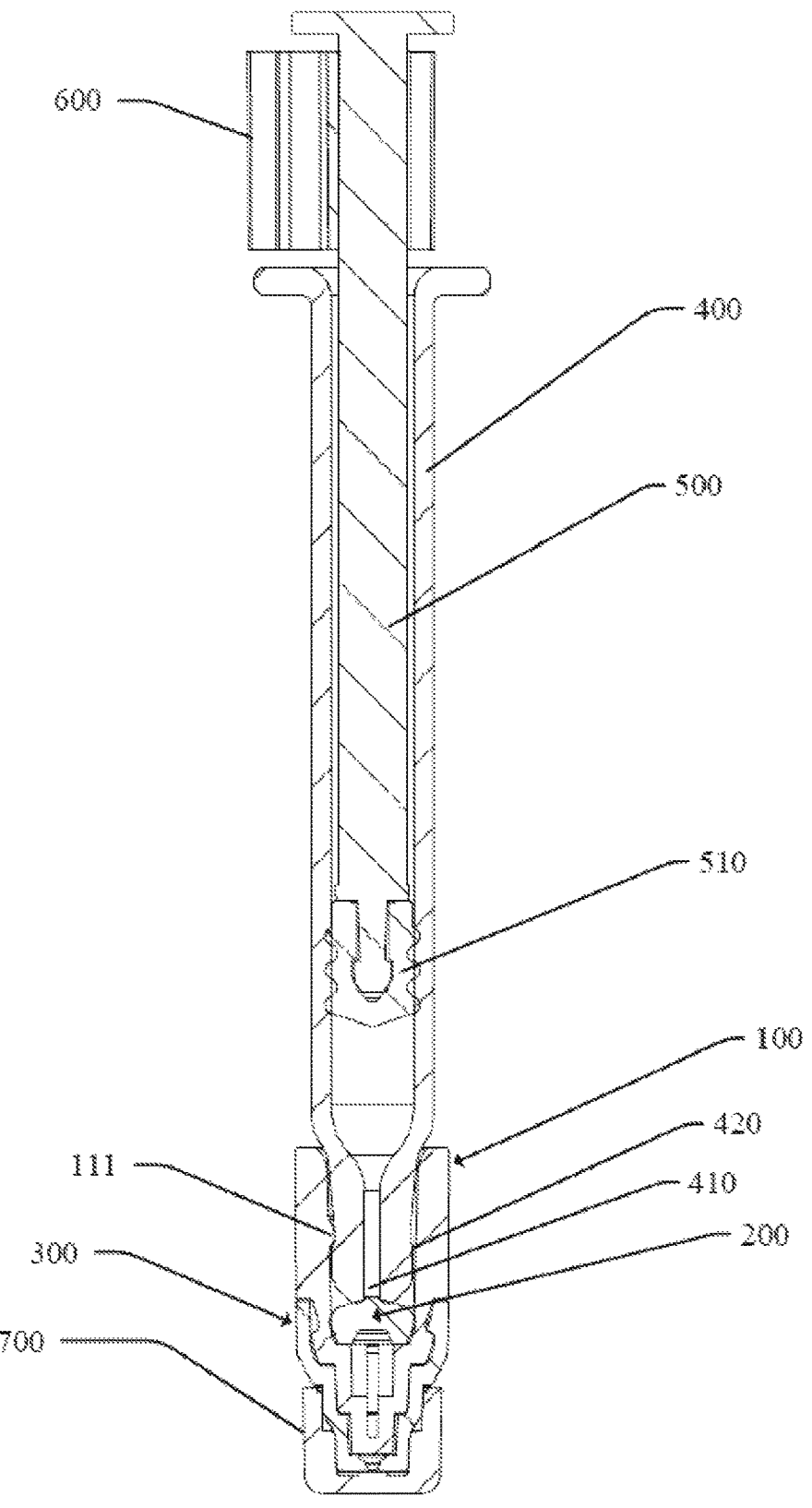
FIG. 6 shows a sectional view of the assembly of the rubber plug, the atomizer, the sprayer and the needle tube according to one aspect of the present disclosure.

FIG. 6 shows a sectional view of a combination of the rubber plug, the atomizer, the sprayer and a needle tube according to one aspect of the present disclosure. As shown in FIG. 6, during use, a front end of the needle tube 400 extends into the atomizer inner cavity 110 of the atomizer 100 and butts against the umbrella-shaped boss 230 of the rubber plug 200. The liquid outlet 410 of the needle tube 400 is to block by the umbrella-shaped boss 230, and more specifically, by the tip 231 of the umbrella-shaped boss 230.

The outer wall of the front end of the needle tube 400 and the atomizer inner cavity 110 can be bonded and sealed by glue. In an embodiment, the outer wall of the front end of the needle tube 400 is provided with a circle of convex parts 420. Accordingly, one or more buckles 111 are arranged on the inner wall of the atomizer inner cavity 110 of the atomizer 100. The buckles 111 can be matched with the convex part 420 to realize the clamping and positioning between the needle tube 400 and the atomizer 100.

The needle tube 400 may be provided with a push rod 500, and the front end of the push rod 500 may be provided with a piston 510. In an embodiment, a location limiter 600 may be provided between the tail end of the needle tube 400 and the tail end of the push rod 500. As shown in FIG. 6, the nozzle 310 can also be covered with a protective cap 311.

During transportation, the liquid medicine is filled in the cavity between the piston 510 and the liquid outlet 410 in the needle tube 400 and sealed by the piston 510 and the rubber plug 200. When the spray is needed, push rod 500 is pushed forward in the inner cavity of the needle 400, and the liquid medicine in the needle tube 400 flows forward to the liquid outlet 410 under pressure. The liquid medicine extrudes the umbrella-shaped boss 230 of the rubber plug 200 to deform it, creates a gap between the liquid outlet 410 and the umbrella-shaped boss 230, and flows out through the gap between the liquid outlet 410 and the rubber plug. The liquid medicine flows into the annular cavity 210 through the longitudinal notch 140 of the rubber plug, and then flows into the atomizer channel 120 through the notch 140. The liquid medicine then flows out of the opening on the front end 130 of the atomizer and enters the inner cavity of the nozzle 310. Since the front end 130 of the atomizer butts against the spiral protrusion on the inner end surface of the nozzle 310, the liquid medicine passes through the spiral protrusion, in the space between the end surface of the atomizer front end 130 and the inner end surface of the nozzle 310, to the umbrella-shaped inner cavity 320. Due to the function of the spiral protrusion, the liquid medicine finally entering the umbrella-shaped inner cavity 320 is in a vortex state, and then sprayed out in a mist state through the outlet hole 321 of the umbrella-shaped inner cavity 320.

Through the cooperation among the atomizer, the rubber plug and the needle tube, when the thrust of push rod does not reach the set value during the filling process, the transportation process and the use process of liquid medicine, the inner cavity of needle tube will always be in a vacuum state without liquid leakage and overflow.

What is claimed is:

1. A spraying assembly, comprising an atomizer, a sprayer and a rubber plug, wherein an atomizer inner cavity and an atomizer channel located below the atomizer inner cavity are provided in the atomizer, an atomizer end is comprised in a lower part of the atomizer, and a side wall of the atomizer end is provided with at least one opening;

the rubber plug is located at a bottom end of the atomizer inner cavity, an upper end of the rubber plug is provided with an umbrella-shaped boss, an annular cavity is formed between a lower end of the rubber plug and an inner wall of the atomizer, the rubber plug is provided with at least one longitudinal notch along a circumferential direction to connect the annular cavity and a space above the rubber plug, and the bottom end of the atomizer inner cavity is provided with at least one notch to connect the atomizer channel and the annular cavity;

the sprayer comprises a nozzle, the atomizer end of the atomizer extends into a nozzle inner cavity of the nozzle, the at least one opening on the atomizer end connects the atomizer channel of the atomizer to the nozzle inner cavity, a bottom of the nozzle is provided with an umbrella-shaped inner cavity, and an outlet hole is arranged in center of a head of the umbrella-shaped inner cavity.

2. The spraying assembly of claim 1, wherein a diameter of the lower end of the rubber plug is smaller than that of the atomizer inner cavity to form the annular cavity between the lower end of the rubber plug and the inner wall of the atomizer.

3. The spraying assembly of claim 1, wherein a middle part of the rubber plug is provided with a convex part along an outer circumference, and the convex part contacts with an inner wall of the atomizer inner cavity.

4. The spraying assembly of claim 3, wherein the convex part is a hemispherical or tapered convex structure.

5. The spraying assembly of claim 1, wherein the rubber plug is made of elastic material.

6. The spraying assembly of claim 5, wherein the elastic material comprises isobutylene isoprene rubber, nitrile butadiene rubber, silica gel, rubber, TPE, TPU or PVC.

7. The spraying assembly of claim 1, wherein a profile angle of a cross section of the umbrella-shaped boss is $142°±37°$.

8. The spraying assembly of claim 1, wherein a circle-shaped fastening section is arranged above the atomizer end, and an outer side of the fastening section is interference fit with an inner wall above the nozzle of the sprayer to realize sealing.

9. The spraying assembly of claim 8, wherein a circle-shaped convex part is arranged above the fastening section of the atomizer along an outer circumference, the inner wall of the sprayer is provided with at least one convex buckle, and the buckle and the convex part realize closure of the atomizer and the sprayer.

10. The spraying assembly of claim 1, wherein a spiral boss is arranged around the umbrella-shaped inner cavity on an inner end surface of the nozzle.

11. The spraying assembly of claim 1, further comprising:

a needle tube, a front end of which extends into the atomizer inner cavity of the atomizer and butts against the umbrella-shaped boss of the rubber plug, wherein a liquid outlet of the needle tube is blocked by the umbrella-shaped boss; and a push rod, arranged in the needle tube, and having a piston installed at a front end thereof.

12. The spraying assembly of claim 11, further comprising:

a protective cap for protecting the nozzle, wherein a location limiter is arranged between a tail end of the needle tube and a tail end of the push rod.

* * * * *